United States Patent [19]

Hawkswell

[11] E Patent Number: Re. 32,538

[45] Reissued Date of Patent: Nov. 10, 1987

[54] HEAD FOR HANDLING ELECTRICAL COMPONENTS

[75] Inventor: Victor T. Hawkswell, Witham, England

[73] Assignee: USM Corporation, Farmington, Conn.

[21] Appl. No.: 11,557

[22] Filed: Feb. 5, 1987

Related U.S. Patent Documents

Reissue of:

[64] Patent No.: 4,624,050
Issued: Nov. 25, 1986
Appl. No.: 776,972
Filed: Sep. 12, 1985

[30] Foreign Application Priority Data

Jan. 23, 1984 [GB] United Kingdom ..... 84/00015

[51] Int. Cl.[4] ..... B65G 47/91; H05K 13/02

[52] U.S. Cl. ..... 29/740; 29/26 A; 29/743; 294/2; 294/64.1; 414/226; 414/737; 414/752; 414/744 B

[58] Field of Search ..... 29/26 A, 558, 568, 740, 29/741, 743, 760; 294/2, 64.1; 414/737, 744 B, 752, 226; 901/40

[56] References Cited

U.S. PATENT DOCUMENTS

| | | | |
|---|---|---|---|
| 3,676,911 | 7/1972 | Austin | 29/558 |
| 4,135,630 | 1/1979 | Snyder et al. | 414/737 |
| 4,290,732 | 9/1981 | Taki et al. | 414/752 |
| 4,346,514 | 8/1982 | Makizawa et al. | 29/740 |
| 4,381,601 | 5/1983 | Tamai et al. | 29/743 |
| 4,437,232 | 3/1984 | Araki et al. | 414/737 |
| 4,451,976 | 6/1984 | Fujita et al. | 29/740 |
| 4,473,247 | 9/1984 | Itemadani et al. | 414/752 |
| 4,505,020 | 3/1985 | Kinoshita | 29/26 A |
| 4,515,507 | 5/1985 | Asai et al. | 414/744 B |
| 4,611,397 | 9/1986 | Janisiewicz et al. | 29/740 |

FOREIGN PATENT DOCUMENTS 0014940 9/1980 European Pat. Off. .

*Primary Examiner*—Robert L. Spruill
*Assistant Examiner*—Donald R. Studebaker
*Attorney, Agent, or Firm*—William F. White

[57] ABSTRACT

A pick-up head especially for use in a machine for placing electrical components on a substrate comprises a tool holder mounted for movement, conveniently by a lead screw driven by a motor, between a plurality of datum positions and further positions remote therefrom, having means for interchangeably mounting a pick-up tool with a datum face of the tool located at a predetermined position relative to the tool holder. The head further comprises a plurality of orienting jaws mounted for movement towards and away from a component carried on the datum face of a tool on the tool holder when the holder is in one of the datum positions whereby the jaws can engage the component to orient the component. The jaws have a plurality of spaced sets of cooperating datum faces disposed generally transversely to the plane of the datum face of the tool in the holder, each set of datum faces being disposed so as to be capable of orienting a component carried by a tool mounted on the tool holder when the holder is at a corresponding one of said datum positions. A machine including the pick-up head comprises a tool support for supporting a plurality of tools and the machine is arranged so that tools carried by the pick-up head may be interchanged with tools in the tool support dependent upon the components which are to be handled. A wide range of components sizes can be handled using the single pick-up head.

23 Claims, 9 Drawing Figures

112
118
116
214
116
114
114
110
110
116
116
118
118
112

HEAD FOR HANDLING ELECTRICAL COMPONENTS

Matter enclosed in heavy brackets [ ] appears in the original patent but forms no part of this reissue specification; matter printed in italics indicates the additions made by reissue.

FIELD OF THE INVENTION

This invention relates to heads for handling electrical components, for example so-called "chips", flatpacks, S.O. style transistors, leadless chip carriers and the like, and to machines for handling electrical components comprising such heads.

BACKGROUND OF THE INVENTION

It is necessary to handle electrical components for a variety of purposes in modern technology. One major area in which many components have to be handled is the application of components to substrates, for example printed circuit boards, in the assembly of electronic circuitry. In the handling of electronic components, specially in placing various components on printed circuit boards, it is essential that the components be positioned precisely at a desired location and in a desired orientation. Many machines have been proposed for accurately placing components on substrates. Some of these previously known machines have included so-called pick-up heads by which components are picked up from a component supply and placed in a desired position and orientation on a suitable substrate. U.S. Pat. Nos. 4,135,630 and 4,290,732 both describe machines for picking up electrical components and placing them at desired positions and orientations on a suitable substrate. The pick-up heads of the machines described in each of these U.S. patent specifications have a vacuum or suction tool by which components are held on the pick-up head and so-called pawls or fingers by which the components are positioned accurately in correct orientation on the tool. Machines of this type are capable of very precise positioning of components of appropriate size. However, it is frequently necessary to position a number of components of widely varying sizes on a single substrate. By way of example components to be placed on a single board may have sides ranging from 1.25 mm to 31.5 mm in length and may be up to 6.5 mm in thickness. The heretofore known machines, for example of the type described in the aforementioned U.S. patent specifications, are capable of satisfactorily handling a small range of sizes of components; however, in order to accommodate components of the size variation which it is often necessary to position on substrates, sufficient accuracy and reliability has not been achieved with a single pick-up head without manually adjusting or changing the pawls or fingers, or alternatively providing the components in an already orientated manner. This latter system demands extreme accuracy in delivering components to the pick-up head which requires a component feed means which is dimensionally accurate to very close tolerances and hence which is very expensive—known component feed systems provide components in pockets of reeled tapes or so-called "sticks" in both of which cases it is difficult to ensure that the components supplied are oriented in the component supply sufficiently accurately. In addition, if, in order to achieve sufficiently precise positioning, the component feed is relied on to give the necessary accuracy, there is a considerable period (from picking the components from the component supply to finally placing the components on the substrata) during which the components may be disturbed on the pick-up head thereby losing the orientation and precise positioning of the components. Changing of the pawls or fingers on pick-up heads of the type shown in the aforementioned U.S. patent specifications would be a most inconvenient and time-consuming operation and, furthermore, it is difficult to ensure that the replacement pawls or fingers are sufficiently precisely mounted on the pick-up head—great care is required to achieve the necessary precision. Accordingly, where components of a wide variety of dimensions have been called for on a single substrate it has been customary to present the substrate to a plurality of pick-up heads each capable of handling components of different and complementary size ranges. Precision pick-up heads are expensive and a plurality of heads is, furthermore, wasteful of space.

OBJECTS OF THE INVENTION

It is one of the various objects of the present invention to provide an improved head for handling electrical components and orienting the components, which can deal with a bigger range of sizes of components than has hitherto been conveniently possible with the a head comprising orientation pawls or fingers.

Another object of the present invention is that of providing a machine for handling electrical components including a head capable of handling components having a wider size range than hitherto conveniently possible with a single head.

SUMMARY OF THE INVENTION

The above and other objects are achieved by providing a head for handling electrical components comprising a tool holder, means for moving the holder between a plurality of datum positions and further positions remote therefrom, the holder having means for interchangeably mounting a tool with a datum face thereof positioned at a predetermined position relative to the tool holder, the head further comprising a plurality of orienting jaws mounted for movement towards and away from a component carried by and abutting the datum face of a tool mounted on the tool holder when the holder is in one of the datum positions whereby to engage and orient a component carried by the tool, the jaws having a plurality of spaced sets of cooperating datum faces generally transverse to the plane of the datum face of a tool in the holder, each set of datum faces of the jaws being so disposed as to be capable of orienting a component carried by a tool mounted on the tool holder when the holder is at a corresponding one of said datum positions.

With a head having several sets of orienting jaws, it is possible to handle a wider range of components than with previously known heads. Suitably the tools carried by the holder can be interchanged so that the holder mounts a tool most appropriate for the compoent to be carried by the tool. Preferably the tool holder of a head according to the invention has a socket in which a shank portion of a tool can be received to mount the tool on the holder in a located position, the tool holder being conveniently provided with retaining means to retain the shank of the tool in the socket.

A machine for handling electrical components comprising such a head with interchangeable tools also comprises means facilitating interchanging of the tools. Such a machine comprises a tool support for supporting a plurality of tools and means for relatively moving the head and tool support whereby to mount a preselected tool carried by the tool support on the tool holder. Provision of such a tool support enables a machine for handling electrical components and, for example, placing the components in predetermined positions on substrates, to operate without any intervention during the operative cycle from the operator to handle a wide variety of components.

BRIEF DESCRIPTION OF THE DRAWINGS

There now follows a detailed description to be read with reference to the accompanying drawings, of a component placing machine having a pick-up head embodying the invention. It will be realized that this machine has been selected for description to illustrate the invention by way of example.

In the accompanying drawings

DESCRIPTION OF THE PREFERRED EMBODIMENT

Figure 1:
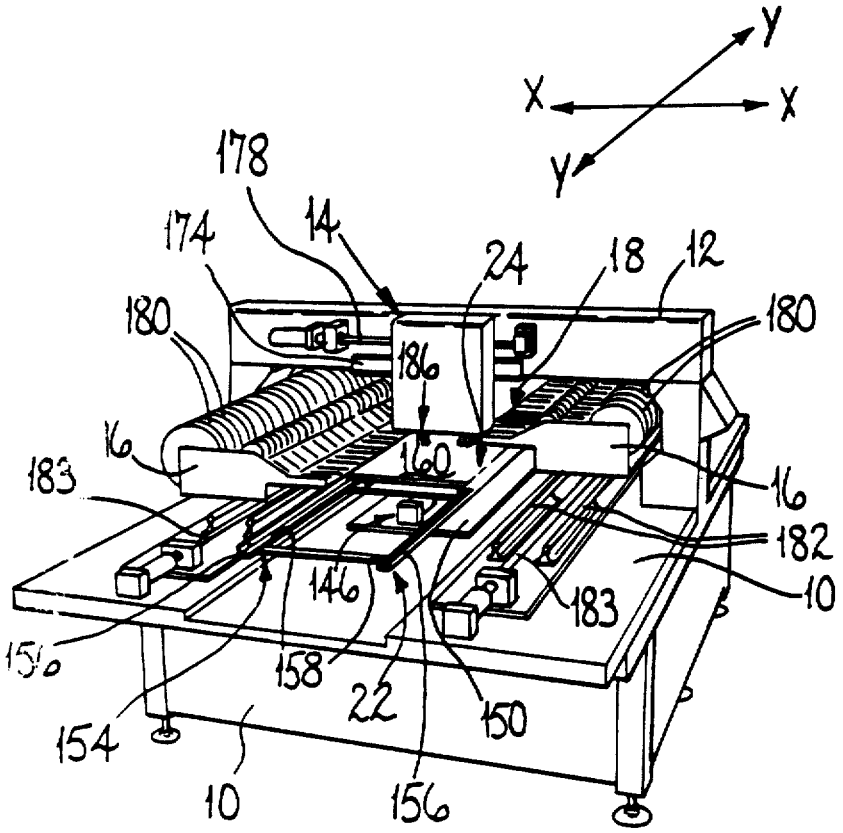
FIG. 1 is a perspective view of the component placing machine.
Figure 2:
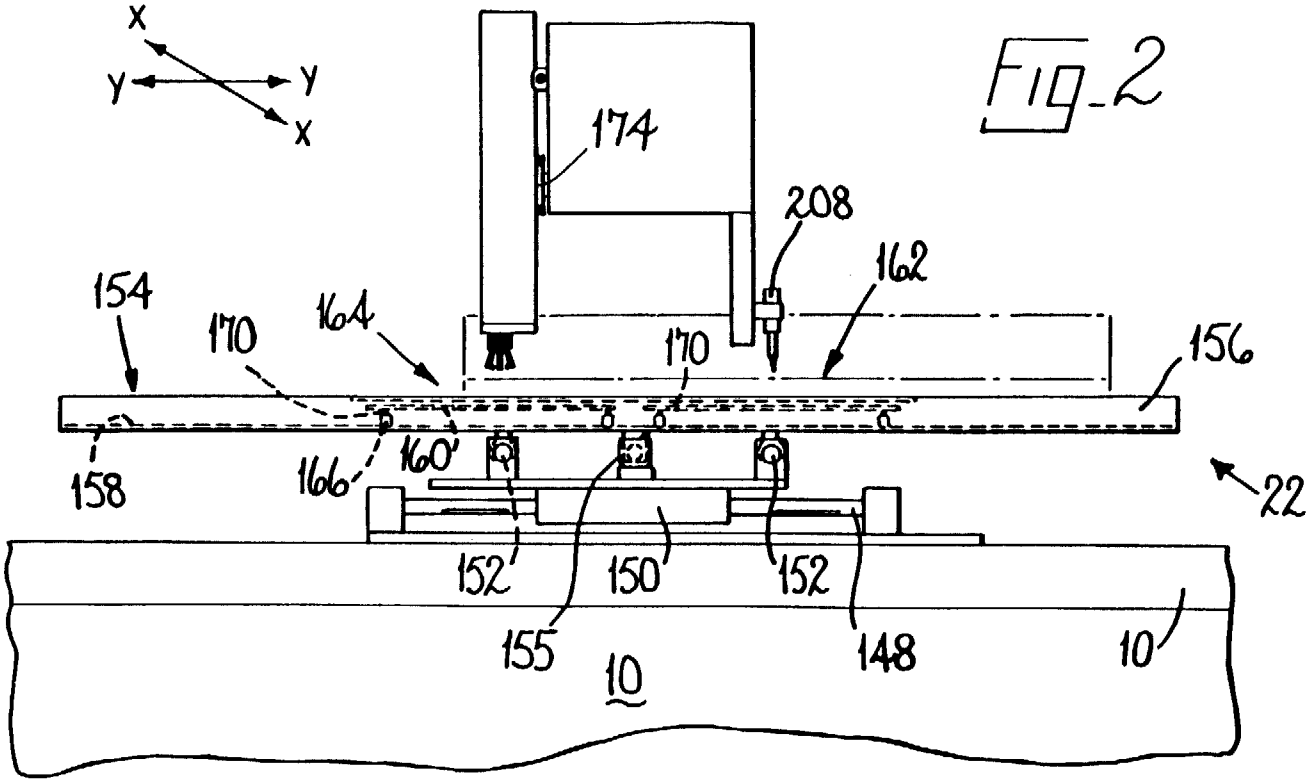
FIG. 2 is a view in side elevation of the machine embodying the invention.

A component placing machine for handling electrical components, for example so-called "chips", and placing them in predetermined positions on a suitable substrate, for example a printed circuit board or boards, embodying the invention, is shown in FIG. 1. The component placing machine comprises a frame 10 including a bridge member 12 on which are mounted twin pick-up heads 14. Two carriages 16 are mounted for movement along parallel paths beneath the bridge member 12, each carriage 16 being associated with one of the pick-up heads 14; on each of the carriages 16 a tool support 18 for supporting a plurality of tools 20 for supply to the associated pick-up head, is disposed. Between the two carriages is mounted a substrate support 22 on which substrates 24, for example printed circuit boards, may be located for placement of electrical components thereon. The machine further comprises means (to be described in greater detail hereinafter) for relatively moving the pick-up heads 14 and tool supports 18 whereby to mount a preselected one of the tools 20 carried by the tool support 18 on a tool holder 26 (see FIG. 3) of the pick-up heads 14.

The pick-up heads 14 are mounted for rotation about spaced vertical axes in bearing 28 carried by support brackets 30 of a head support member 32. The pick-up heads 14 are substantially identical in construction and therefore only one of the heads will be described in detail hereinafter.

This pick-up head comprises a body member 34 which is supported for rotation in the bearings 28. The body member 34 is hollow and a carrier 36 to which is secured a drive nut 38 is mounted for vertical sliding movement within the body member 34. The carrier 36 comprises a guide pin 40 slidable in a vertical keyway 42 in the wall of the body member 34 whereby to prevent rotation of the carrier 36 relative to the body member 34.

A substantially cylindrical vertical bore 46 extends through the carrier 36. The tool holder 26 comprises a shaft portion 44 which is slidingly received in a lower end portion of the bore 46 with the remainder of the tool holder 26 projecting downwardly beyond the carrier 36. A guide pin 48 fixed in the shaft portion 44 is received in a slot 50 in the carrier 36 whereby to prevent rotation of the tool holder 26 relative to the carrier 36 and to restrict the distance by which the tool holder 26 may move relative to the carrier 36 in a vertical direction. The tool holder 26 is normally in a lowermost position relative to the carrier 36, with the guide pin 48 engaging a lowermost end face of the slot 50, remaining in this position under the force of gravity: this lowermost position is a location position of the tool holder 26.

The holder 26 comprises means for interchangeably mounting one of the pick-up tools 20 with a datum face thereof positioned at a predetermined position relative to the tool holder. This mounting means comprises a socket 52 in a lowermost end portion of the tool holder 26 in which a shank 54 of the tool 20 is slidingly received. The tool holder 26 comprises retaining means resiliently biased into a recess 56 in the shank 54 of a tool 20 received in the socket 52 to retain the tool 20 on the holder 26. The retaining means comprises a plurality, vis. a pair, of balls 58 held captive in the holder 26 but projecting into the socket 52, the balls being resiliently biased into the socket 52 by a resilient rubber sleeve 60 surrounding the lower end portion of the holder 26 and operating on portions of the balls 58 projecting from their housing in the holder 26 to urge the balls inwardly of the socket 52. The tool 20 is accurately located at the predetermined position relative to the holder 26 by engagement of a locating face 62 of a projecting collar 64 of the tool 20 with a lowermost location face of the tool holder 26, thus to locate a datum face 66 of the tool 20 relative to the holder 26 so that the datum face 66 is in said predetermined position. A passage 68 extends axially through the tool 20 and opens through the datum face 66. An upper end portion of the passage 68 opens to means for connecting the passage 68 to a vacuum source of the machine, said means being provided by a bore 70 in the tool holder 26 connected by a flexible rubber pipe (not shown) to the vacuum source.

The machine further comprises means for moving the carrier 36, and thus the tool holder 26, vertically between a plurality of datum positions and further positions remote therefrom. The means for moving the carrier 36 vertically comprises a lead screw 72 mounted for rotation coaxially with the body member 34 in bearings 74 carried by a further bracket 76 of the head support member 32 and a bearing 78 at an upper end portion of the body member 34; the lead screw 72 is fixed against vertical movement by lock nuts 80 and a circlip 82. A threaded portion of the lead screw 72 is received in the drive nut 38 so that rotation of the lead screw 72 in the drive nut 38 causes vertical movement of the drive nut (thus the carrier to which it is fixed) relative to the body member 34 which is fixed against vertical movement in the bearings 28. Thus, when the tool holder 26 is at its lowermost position relative to the carrier 36 the tool holder may be moved by rotation of the lead screw 72 between a plurality of datum positions and further positions remote therefrom.

The lead screw 72 is arranged to be driven by a servo motor 84 mounted on the head support member 32: a pulley 88 secured to an output shaft of the servo motor 84 drives, through a toothed drive belt 86 a pulley 90 keyed to the lead screw 72. An encoder 92, also mounted on the head support member 32, likewise driven by the output shaft of the servo motor 84, provides a digital indication of the rotation of the output shaft of the servo motor 84 and thus of the pulley 90 and the lead screw 72 to which it is keyed: this information is used by a computer control sytem of the machine to control the rotation of the lead screw 72 whereby to control a vertical position to which the carrier 36 is moved.

As hereinbefore mentioned, the whole pick-up head 14 is rotatable in the bearings 28. A gear 94 is secured to the body member 34 of the pick-up head 14; the gear 94 is in mesh with a gear 96 secured to the output shaft of a stepping motor 98. As is well known stepping motors are constructed to be rotated through a known angle each time a pulse is received by the motor: thus, by supply of a known number of pulses the stepping motor may be rotated through a known angle. In the case of the stepping motor 98, by causing the output shaft of the motor 98 to rotate through a previously determined angle by supply of the requisite number of pulses, the body member 34 may likewise be rotated through a predetermined angle. As the carrier 36 is constrained to rotate with the body member 34 and the tool holder 26 is likewise constrained to rotate with the carrier 36, operation of the stepping motor 98 to rotate it through a predetermined angle will cause rotation of the tool holder 26 through a predetermined angle, likewise. However, rotation of the carrier 36 and thus the drive nut 38 which is secured thereto, whilst the lead screw 72 remains fixed, will cause a change in the height of the carrier 36 relative to the body member 34. A clutch mechanism 100 is therefore provided which operates on a signal from a computer control of the machine just prior to operation of the stepping motor 98, to effectively clamp together the lead screw 72 and the body member 34 so that when the stepping motor 98 operates to rotate the body member, the lead screw rotates with the body member as one unit. After the stepping motor 98 has rotated through the desired angle, the computer control signals release of the clutch mechanism 100 so that the lead screw 72 and body member 34 can again rotate independently of one another. The inertia provided by the stepping motor 98 together with the gears 94, 96 is sufficient to maintain the body member 34 in the position to which it has been rotated.

Figure 3:
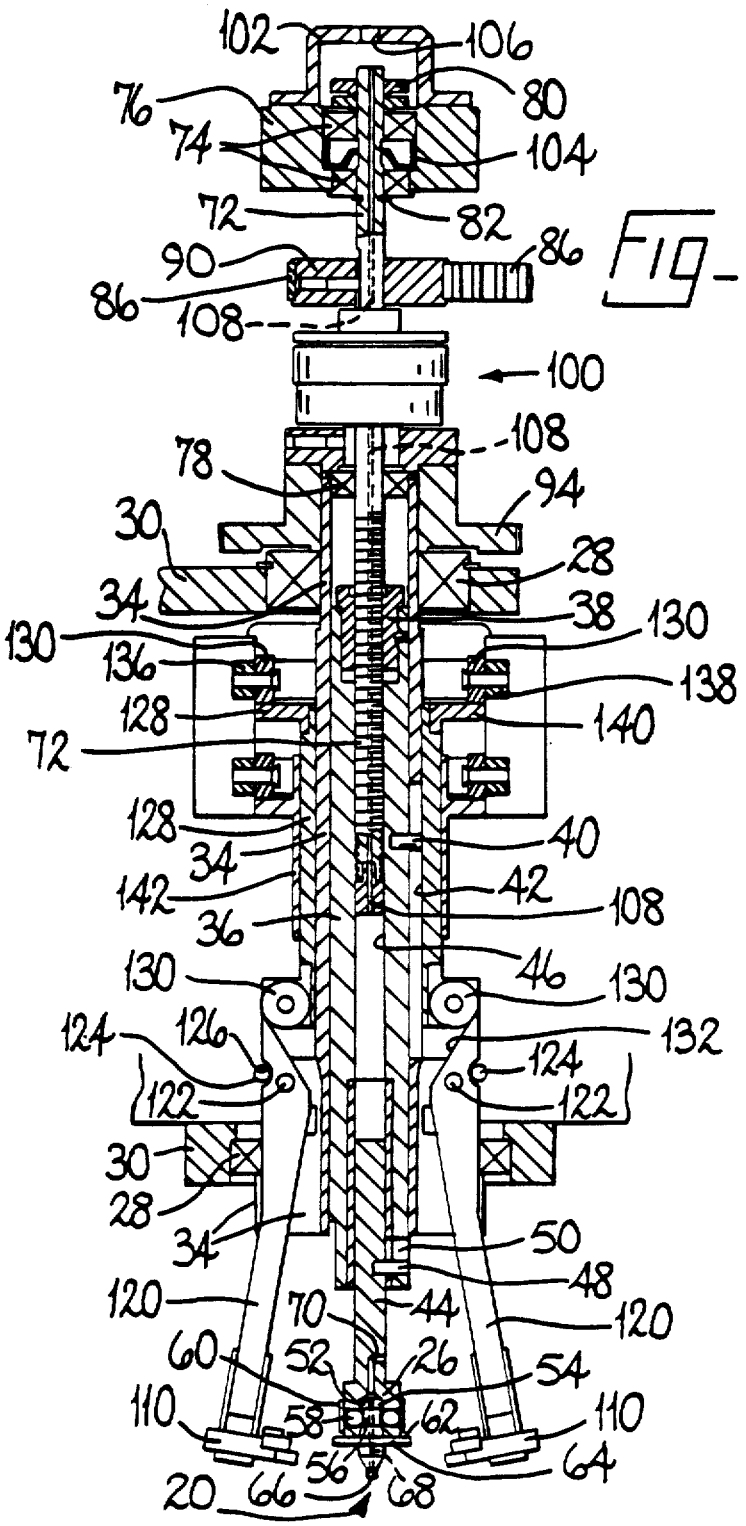
FIG. 3 is a view in section showing part of the pick-up head.

A bearing cap 102 is sealed in an air-tight manner to the further bracket 76 enclosing an upper end portion of the lead screw 72; an air-tight gasket 104 seals around the lead screw 72 towards a lower portion of the bracket 76. A passage 106 in the bearing cap 102 allows air under pressure to be introduced to the chamber formed between the bearing cap 102 and the bracket 76. A passage 108 extends longitudinally along the lead screw 72 and opens at the lower end into the bore 46 in the carrier 36 above the upper end portion of the shaft portion 44. A lower end portion of the lead screw provides a sliding seal against the bore 46 of the carrier and likewise the shaft portion 44 provides a sliding seal in the bore 46. Thus air under pressure introduced through the passage 106 enters the bore 46 via the passage 108 to act on the shaft portion 44 of the tool holder 26 to urge to its lowermost, location position (in which it is shown in FIG. 3). The air pressure which may be supplied through the passage 106 may be adjusted to apply a preselected pressure on the tool holder 26 for a reason to be discussed hereinafter.

The pick-up head 14 further comprises a plurality of, viz. two, oppositely disposed pairs of orienting jaws 110, 112 mounted for movement towards and away from a component (not shown) carried by and abutting the datum face 66 of a tool 20 mounted on the tool holder 26 when the holder is in its lowermost, location position whereby to engage and orient the component. The jaws 110, 112 have a plurality of vertically spaced sets 114, 116, 118 of cooperating datum faces which are disposed generally transversely to the plane of the datum face 32 of the tool 20 in the holder 26. Each of these sets 114, 116, 118 is disposed so as to be capable of orienting a component carried by a suitable tool 20 positioned against the tools datum face 66 of the tool, when the tool holder 26 is located in a corresponding one of the datum positions of the holder by appropriate rotation of the lead screw 72 to move the carrier 36 and thus the tool holder 26 to the appropriate datum position. The tool 20 used is selected to be of most appropriate construction for handling the particular component in question, the datum positions of the holder 26 being selected so that the datum face 66 of the appropriate tool will be appropriately positioned vertically so that a component abutting the particular face 66 will be in register with the appropriate one of the sets 114, 116, 118 of datum faces of the jaws 110, 112.

Figure 6:
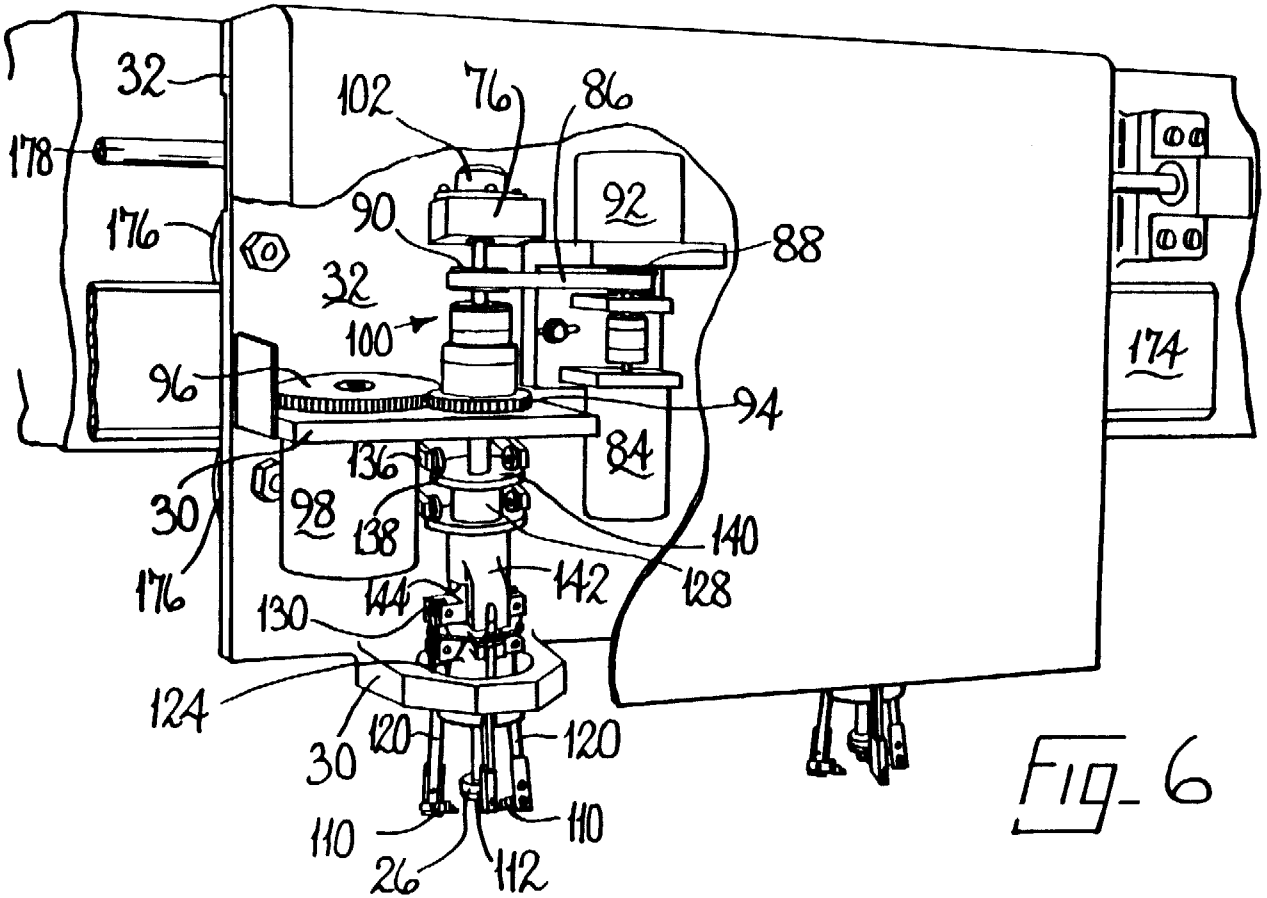
FIG. 6 is a view in front elevation of part of the machine showing twin pick-up heads of the machine with a cover partly broken away.

As can be seen from FIGS. 3 and 6, the jaws 110, 112 are secured in an accurate location at lowered portions of arms 120 which are pivotally mounted by pivot pins 122 carried by parts of the body member 34. The arms 120 mounting an opposed pair of the jaws 110, 112 are mounted for pivotal movement about horizontal, parallel axes the axes relating to the jaws 110 being disposed at rightangles to the axes relating to the jaws 112. The arms 120 are biased outwardly by a tension spring 124 of generally circular form extending around upper end portions of the arms 120 in grooves 126 therein. Each pair of jaws 110, 112 may be moved in synchronism towards one another by similar means of which only the means operating the pair of jaws 110 will be described in detail. Each pair of jaws may be operated independently of the other pair of jaws.

The means for moving the jaws 110 inwardly towards one another (and towards a component carried by a tool 20 in the holder 26 when the holder is in its datum position) comprises a slide member 128 mounted for sliding movement up and down an outer bearing portion of the body member 34. A pair of rollers 130 is mounted for rotation on the slide member 128 and engage inclined upper end faces 132 of the arms 120 carrying the jaws 110. Thus, when the slide member 128 is forced downwardly, the rollers 130 slide down the inclined upper end faces 132 and force the upper end portions of the arms 120 outwardly against the action of the tension spring 124, thereby pivoting the jaws 110 inwardly towards one another. When the slide member 128 is lifted, the rollers move upwardly along the faces 132 thereby allowing the spring 124 to urge the upper end portions of the arms 120 inwardly, pivotting the jaws 110 apart. The slide member 128 may be arranged to be raised positively by suitable means or may merely be lifted by action of the spring 124 upon removal of downward pressure from the slide member. The slide member 128 is arranged to be moved by means of a corresponding piston and cylinder arrangement (not shown) carried by the head support member 32 and arranged to operate on a lever 136 pivoted on the support member 32. A roller 138 carried by an end portion of the lever 136 remote from the piston and cylinder arrangement 134 bears on a collar 140 of the slide member 128. Thus operation of the piston and cylinder arrangement pushes an end portion of the lever 136 adjacent the arrangement upwardly causing the roller, 138 to move downwardly thereby urging the slide member 128 downwardly and thus the jaws 110 towards one another. Means for operating the other pair of jaws 112 is generally similar except that a slide member 142 thereof generally corresponding in function to the slide member 128 is arranged to slide on an outer bearing surface provided by the slide member 128 itself and has two recesses 144 at a lower end portion thereof to accommodate the rollers 130 carried by the slidemember 128. The slidemember 142 is operated by further piston and cylinder arrangement (not shown) in similar manner to operation of the slide member 128. Thus by appropriate timing of the operation of the piston and cylinder arrangements operation of the pairs of jaws 110, 112 may be timed to occur at an appropriate moment, or indeed it is possible to cause only one of the pairs of jaws to operate in appropriate circumstances, for example when the component to be handled is of cylindrical shape, in which case the component would be carried by an appropriate tool grooved to receive the cylinder and only one pair of arms would be used operating upon opposite end portions of the cylinder component (a so-called "Melf" component) to both align the component lengthwise in the tool and to orient the tool about the vertical axis of tool holder precisely (it will ordinarily have been picked up in substantially the correct orientation when loaded into the tool holder 26).

The substrate support 22 is generally of previously known construction and comprises a so-called X-Y table having longitudinal rails 148 mounted on the frame 10 on which a carriage 150 slides lengthwise of the machine, i.e. in the Y direction. The carriage 150 is arranged to be driven along the rails 148 by means of a suitable drive mechanism 146 e.g. a Rohlex drive under the control of computer means of the machine. An optical position determination system of known construction is disposed to indicate to the computer means the precise position of the carriage 150. Transverse rails 152 are secured on the carriage and support means 154 are mounted for sliding movement along the rails 152 transversely of the machine, i.e. in the X direction. The support means 154 is arranged to be driven along the rails 152 to and fro in the X direction by a suitable drive means 155 e.g. a Rohlex drive system; an optical detection means of known construction is mounted on the carriage 150 to indicate to the computer means the position of the support means 154 transversely of the machine i.e. in the X direction. By operation of the two Rohlex drive systems, moving the support means 154 in the X direction and the carriage 150 (and with it the support means 154 mounted thereon) in the Y direction, the support means can be moved through a full range of operative positions.

The support means comprises a pair of parallel rail members 156 which are horizontal and extend in the Y direction and which provide two upwardly facing support surfaces 158 on which pallets 160 may be mounted. Substrates 24, on which components are to be placed, are mounted on the pallets 160 for presentation to the operative instrumentalities of the machine in precisely known locations relative to datum positions of the pallets 160. Each pallet has two location holes therein at diagonally opposite corners thereon, one of the two holes being the datum position of the pallet. The pallets 160 can be located on the support surfaces 158 of the support means 154 in one of two stations—a first, adhesive dispensing station 162 or a second, placement station 164. At each of the two stations 162, 164 are disposed locating means by which substrates can be located at the respective one of the stations 162, 164 and clamp means by which the substrates may be clamped in the station. The locating means and clamp means at each station 162, 164 are identical and for convenience only those at the station 162 will be described hereinafter. The locating means comprises two spaced pneumatic cylinders 166 (only one visible on drawings) secured to the support means 154 with piston rods 170 thereof arranged to project upwardly therefrom. The cylinders 166 are mounted one on each of the rail members, positioned to register with the location holes of a pallet. When a pallet 160 is to be placed in the adhesive dispensing station it is rested on the support surfaces 158 of the rail members 156 and moved into position with the location holes substantially aligned with the piston rods 170 which at this time are retracted within the cylinders 166; when the pallet has been placed in this position, the cylinders 166 are actuated to extend the piston rods 170 from the cylinders 166 so that conical, guiding, leading end portions of the rods enter the holes in the pallets 160. The main body of the piston rods 170 below the leading end portions is cylindrical and accurately machined and the cylinders 166 are accurately located on the support means 154. The cylindrical portion of the piston rod 170 of the leading pneumatic cylinder 166 is arranged to slidingly engage in a circular hole (the datum position hole) in the leading end portion of the pallet 160 and the piston rod 170 of the trailing cylinder 166 ( not visible in the drawings) is arranged to enter an oval hole which is slightly elongated in the Y direction (considered when the pallet is in the machine) but of the same width as the diameter of the leading hole. Thus the leading cylinder 166 cooperating with the leading hole of the pallet 160 locates the leading end portion of the pallet and the trailing hole and the trailing cylinder locates the pallet in angular orientation about the leading hole. The pallets 160 are of rigid construction, all of similar dimensions. Datum surfaces which locate the pallets 160 in the vertical direction (the Z direction) are provided by overhanging lips of the rail members 156 at each of the stations 162, 164. The clamp means at each station 162, 164 comprise two pneumatic cylinders 168 mounted on the rail members 156 positioned to register with those diagonally opposite corners of a pallet 160 located by the locating means in which the locating holes are not disposed. On activation of the cylinders 168 (after a pallet has been located by the cylinders 166) piston rods of the cylinders 168 are moved into engagement with the associated corners to raise the upper surface of the pallet into engagement with and clamp the pallet against the datum surfaces of the lips; thus, an upper surface of the pallet is located accurately in the Z direction so that the height in the Z direction at which components are to be placed can be included in the information supplied to the computer means.

The pallets 160 may support one or several printed circuit boards in known positions relative to the datum point of the pallet; should the board on which components are to be placed already carry any component or other structure projecting below a lower surface of the substrate, appropriate openings may be made in the pallet 160 to accommodate the projecting portions. Alternatively the substrate 24 may, itself, be a printed circuit board of suitable dimensions, provided that the board is sufficiently rigid, in which it is not necessary to use a pallet.

The machine embodying the invention described herein comprises two pick-up heads 14 as hereinbefore mentioned, the heads being mounted on the head support member 32 which itself is mounted for sliding movement transversely of the machine (in the X direction) on the bridge member 12 of the frame 10, above the substrate support 22. The head support member 32 is mounted for sliding movement on a rail system 174 secured to the bridge member 12: wheels 176 mounted for rotation on the head support member 32 run on the rail system 174 whereby to permit the said sliding movement. The head support member 32 is moved along the rail system 174 by a Servo motor which rotates a shaft 178 mounted for rotation on the bridge member 12 and drives the head support member 32 through a Rohlex drive mechanism. The position of the head support member 32 transversely of the machine (in the X direction) and thus of the pick-up heads 14 carried by the member 32 is verified by an optical encoder system (not shown).

As hereinbefore mentioned the carriages 16 on which component supply magazines 180 and the tool supports 18 are carried are mounted one at either side of the substrate support 22. Each of the carriages 16 is mounted for sliding movement (in the Y direction) on rails 182, the carriages being arranged to be moved by shafts 183 driven by motors, through Rohlex drive mechanisms. Suitable rotary encoders driven by toothed belts on the carriages, are associated with each carriage to indicate the precise position of the carriage 16 in the Y direction of the machine to the computer means. Each of the carriages 16 mounts a plurality of component supply magazines 180 of known type, for example tape feed magazines in which sticks are carried in pockets in a reeled tape, so-called "stick" feed magazines or vibrating trough feeders. Each carriage 16 may be moved on the rails 182 to present a component at an outlet position of any selected one of the magazines 180 mounted on the carriage 16 at a pick-up position associated with one of the pick-up heads 14. By movement of the head support member 32 along the bridge member 12 one of the heads 14 associated with one of the pick-up positions may be moved between a placement position 186 (in which the head is arranged to place a component upon a substrate carried on the substrate support) and a position remote from the placement position adjacent the associated pick-up position to pick-up components therefrom. As discussed previously, tools carried by each of the pick-up heads 14 can be moved vertically in the Z direction, by operation of the lead screw 72, both to pick-up components at the pick-up position and to place components on a substrate when the appropriate head 14 is in the placement position 186. The two heads 14 are mounted side by side, spaced apart in the X direction by a distance such that when one of the heads 14 is in the placement position 186, the other of the heads is disposed in register with its associated pick-up position: thus when the tool holder 26 of a head 14 in the placement position 186 descends to place a component on a circuit board carried by a pallet 160 located at the placement station 164, the holder 26 of the head 14 in register with its associated pick-up position may also descend to pick-up a component from the outlet of a magazine 180 disposed at the pick-up position. Having respectively placed and picked-up components the two tool holders 26 may be raised and the head support member 32 moved in the X direction to bring the one of the heads 14 now carrying a component to the placement position 186 and to move the other head 14 above its associated pick-up position to pick-up a further component for subsequent placement. It will be realized that each head 14 moves to precisely the same placement position 186 to place its component. The substrate support 22 is moved by the X-Y table arrangement so that any preselected point in the work area of a pallet substrate 24 mounted in the placement station 164 can be moved into register with the head in the placement position 186.

As has been mentioned previously, a tool support 18 for an associated pick-up head 14 is carried on the appropriate one of the two carriages 16: the tool supports are both mounted at intermediate positions about halfway along the carriage 16. Each tool support 18 comprises a base 188 secured to the carriage 16 and slide member 190 mounted for sliding movement on an upper surface of the base 188. The slide member 190 is retained on the base 188 by headed pins 192, the pins passing through slots 194 in the slide member, 190 whereby to guide the slide member 190 for sliding movement in the X direction. The slide member 190 can be moved in the X direction by a piston and cylinder arrangement 196 mounted on the frame 10, through a linkage mounted on the carriages 16 to the extent permitted by the headed pins 192 in the slots 194.

Figure 4:
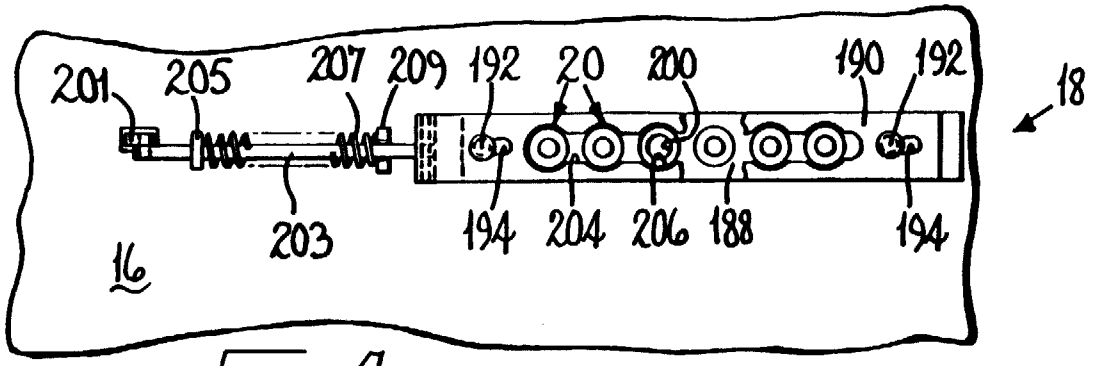
FIG. 4 is a plan view of part of a carriage of the machine showing a tool support thereof.
Figure 5:
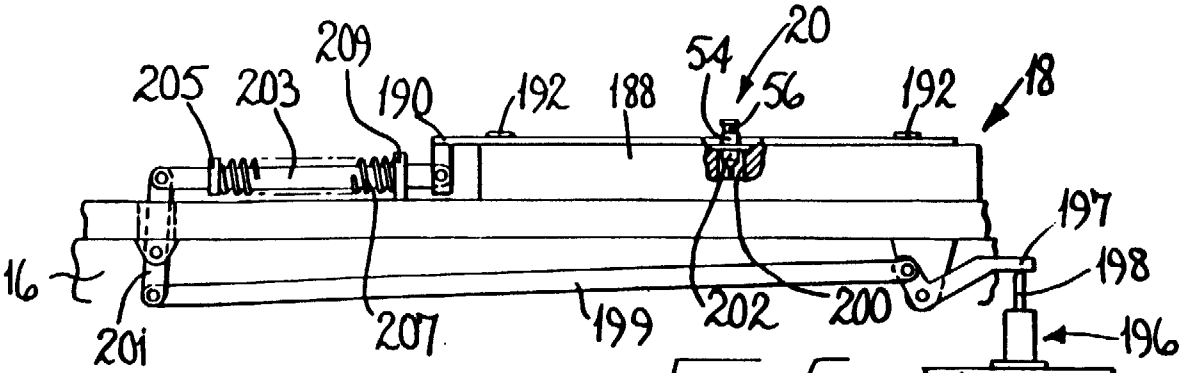
FIG. 5 is a front view showing the tool support of the FIG. 4.

The linkage comprises a two arm lever 197 pivotally mounted on the carriage 16 and so positioned that when the carriage is so positioned on the rail 182 that the tool support 18 is at a tool-loading position, corresponding with the pick-up position of the magazines 180, one arm of the lever is aligned with a piston rod 198 of the piston and cylinder arrangement 196. The other arm of the lever 197 is pivotally connected to one end portion of a link 199 the other end portion of which is pivotally connected to one end portion of a lever 201 pivotally mounted on the carriage remote from the arrangement 196. The other end portion of the lever 201 is pivotally connected to a connecting rod 203, itself pivotally connected to a bracket depending from the slide member 190. A spring 207 round the connecting rod 203 is interposed between a collar 205 fixed to the rod and a guide 209 for the rod 203 fixed to the base 188. The spring 207 urges the slide member to the left (viewing FIGS. 4 and 5). When the tool support 18 is at the pick-up position and the piston and cylinder arrangement 196 is operated to extend the piston rod 198 into engagement with said one arm of the lever 197 whereby to move the lever 197, the linkage arrangement causes the slide member 190 to move to the right viewing FIG. 4 to the position in which it is shown in FIG. 4, compressing the spring 207; when the piston rod 198 is retracted the spring 207 returns the slide member 190 to the left from the position in which it is shown in FIGS. 4 and 5.

A plurality of cylindrical recesses 200 are formed in the base 188, having their centres spaced along a line lying in the X direction. The recesses 200 are dimensioned to receive a nose 202 which projects from the collar 64 of a tool 20 at the opposite side of the collar 64 to the shank 54. Additionally the uppermost surface of the base 188 is recessed to accommodate the collar 64 of the tool 20. The slide member 190 has a slot 204 therein extending in the X direction, the slot 204 being sufficiently wide at all parts to permit the shanks 54 of tools 20 accommodated in the recesses 200, to project upwardly through the slot 204. The slot 204 has enlarged portions 206 which are so dimensioned as to allow clearance for the tool 20 to be withdrawn from the recesses 200 through the enlarged portions 206 when the enlarged portions are aligned with the recesses 200. However when the slide member 190 is moved so that the enlarged portions 206 and recesses 200 are not in register, portions of the slide member 190 overlie the collars 64 of tools 20 received in the recesses 200 thereby retaining the tools 20 in the recesses.

The tool support 18 therefore comprises a housing, provided by the base 188, by which tools are supported in a plurality of positions, viz. in the recesses 200, with their shanks 54 projecting. The means for moving the tool holders 26 which includes means for moving the pick-up heads 14, and for moving the carriages 16 provide means for relatively moving the tool holders 26 and tool support 18 which are effective in the operation of the machine to engage the shank 54 of one of the tools 20 from a preselected one of the recesses 200 in the socket 52 of the tool holder 26 thus to mount the preselected tool in the holder. By moving the carriage 16 carrying the tool support 18 along a first path (in the Y direction) and by moving the associated one of the pick-up heads 14 along a second path, viz. in the X direction, at rightangles to the first path, the tool holder 26 may be aligned with a preselected one of the recesses 200 of the tool support 18. When so aligned, movement of the tool holder 26 by operation of the lead screw 72, in the Z direction can move the holder 26 into engagement with the preselected one of the tools 20 carried in the preselected recess 200 whereby to mount the tool 20 in the holder 26, or, where a tool is to be deposited from the holder 26, move the holder 26 to place the tool 20 in the preselected recess. When a new tool 20 is to be picked up by the tool holder 26 (a previous tool having been removed) it will be necessary to move the slide member 190 by operation of the piston and cylinder arrangement to align the enlarged portions 206 with the recesses 200 (as shown in FIG. 4) so that a leading end portion of the tool holder 26 can be pushed over the shank 54 with the shank 54 received in the socket 52 until the lowermost face of the holder 26 engages the locating face 62 of the collar 64 and the balls 58 engage the recess 56 in the shank 54. When it is desired to unload a tool 20 from the holder 26, the holder 26 is first aligned by moving the appropriate pick-up head 14 in the X direction and the corresponding carriage 16 in the Y direction, with the particular one of the recesses 200 designated for the particular tool 20 to be unloaded. The slide member 190 is moved to align the enlarged portions 206 with the recesses 200 and the tool holder 26 is lowered to place the particular tool 20 in its appropriate recess. With the tool holder 26 still lowered the pressure is removed from the piston and cylinder arrangement 196 and the slide member 190 is returned by action of the spring 207 so that the enlarged portions 206 are moved out of alignment with the recesses 200 and portions of the member 190 slide over the collars 64. The holder 26 is then raised and the balls 58 leave the recess 56, being forced outwardly of the socket 52 against the resilient biasing provided by the rubber sleeve 60: means (not shown) may be provided to assist separation of the tool from the holder in addition to the action described above, if necessary. From the above it will be appreciated that various tools 20 carried by the tool support 18 may be interchanged for one another during a cycle of operation of the machine, provided that the machine is programmed to carryout the necessary movements. In order to pick-up a tool from or return a tool 20 to its appropriate recess 200 it is necessary to move the head into alignment with the appropriate recess 200. As the recesses 200 are spaced apart in the X direction, the one of the pick up heads not aligned with the tool support 18 will be disposed above the substrate support but not normally at the placement position 186 as most of the recesses will not be suitably positioned to permit this. Thus when a tool change is taking place, the pick-up head 14 not involved in the change will remain idle.

The piston and cylinder arrangement 196 is also arranged to operate the component supply magazines 180. For example, in order to feed a component in a tape feeder magazine to the outlet position of the magazine it is necessary to index the tape forward by the distance between adjacent components: a feed system, comprising a linkage on the magazine is arranged to do this. The linkage is so constructed that when a magazine 180 is positioned by movement of the carriage on which it is supported in the pick-up position an actuating lever of the linkage is positioned in register with the piston rod 198 of the piston and cylinder arrangement 196. The arrangement 196 is operated under control of the computer means at the appropriate time in the operation of the machine to index the component supply tape through one feed step thus to move a component to the outlet of the magazine for picking up by the associated pick-up head.

An adhesive dispenser 208 is mounted on the bridge member 12, at the opposite side to the head support member 32, above the adhesive dispensing station 162. The adhesive dispenser 208 is mounted for movement vertically, in the Z direction, but cannot move in the X or Y directions. The adhesive dispenser comprises a container of known construction in which a quantity of a suitable adhesive, for example an epoxy adhesive is contained. The dispenser 208 is arranged so that drops of adhesive may be expelled from a nozzle thereof by pneumatic operation, in known manner. The adhesive dispenser 208 can be used to apply adhesive to a substrate mounted on the support 22 in the adhesive dispensing station 162 at any desired position in the work area of the adhesive dispensing station 162, the X-Y table of the substrate support 22 being operated to move the appropriate point on the substrate 24 into register with the adhesive dispenser 208. The adhesive dispensing station 162 and placement station 164, and the adhesive dispenser 208 and placement position 186 are disposed in relation to one another such that a pick-up head 14 at the placement position 186 places a component on the same position on the work area of a pallet 160 mounted in the placement station 164 on the substrate support 22, as the adhesive dispenser 208 places a drop of adhesive on the work area of a pallet 160 carried by the support 22 in the adhesive dispensing station 162. Thus if both of the pallets 160 at the adhesive dispensing station 162 and the placement station 164 carry an identical array of substrates 24 the placement head 14 at the placement position 186 places its component at the same position on a substrate in the station 164 as a drop of adhesive is placed on the corresponding substrate at the station 162. To achieve the necessary register between the positions in this case it will be necessary to mvoe the X-Y table only to one position and then to activate a head at the placement position 186 and the adhesive dispenser 208 simultaneously, thereby improving the throughput rate of the machine. When all of the electrical components have been placed on substrates 24 carried by a pallet 160 in the placement station 164 the pallet 160 is removed and replaced by a pallet 160 which had previously been disposed in the adhesive dispensing position 162 and on which adhesive was placed by the dispenser 208 as the components were placed on the preceding pallet at the placement position 164.

The tool holders 26 further comprise a detector which detects whether or not a tool 20 is present on the holder 26 when a component is to be picked up during the operation of the machine. Detector means (not shown) are also associated with the vacuum supply to the passage 68 which can detect whether or not a tool 20 in the holder 26 has succeeded in picking up a component at the pick-up position; other forms of detector for checking whether or not components have successfully been picked up (and placed on a substrate) may be used if desired instead of the detector means in the vacuum system referred to above.

As hereinbefore mentioned the operation of the machine is controlled by a suitable electronic computer control system which is programmed by an operator, conveniently by a so-called "walk through" method in which the machine is moved at a slow rate by the operator to perform the necessary sequence of operations which are recorded in a memory for subsequent repetition. Before starting the machine operation it is necessary to first ensure that appropriate tools 20 are accommodated on the tool support 18 on both of the carriages 16 and that the magazines 180 on both carriages contain sufficient of the correct components needed for the assembly operation proposed. Suitable substrates 24 are first mounted in known locations on appropriate pallets and a pallet carrying the substrates mounted on the substrate support 22 in the adhesive dispensing station 162 as described above. The X-Y table is then operated to move the pallet 160 in the adhesive dispensing station 162 to align the adhesive dispenser 208 with positions on the work area of the pallet at which adhesive is to be placed and spots of adhesive are dispensed at the preselected positions on the substrates carried by the pallet. The pallet 160 is then moved from the adhesive dispensing station 162 to the placement station 164 by the operator, at which station the pallet is located; further pallet 160 on which are also mounted substrates 24 in positions corresponding identically with those on the first pallet is then positioned at the adhesive dispensing station 162. The X-Y table is again operated to bring the adhesive dispenser 208 into register with the various preselected positions on the substrates carried by the pallet at the dispensing station 162 and the placement position 186 into register with the corresponding positions on the substrates 24 carried by the pallet 160 at the placement station 164. At each of the preselected positions a drop of adhesive will be placed on the substrate in register with the adhesive dispenser 208 and/or a component will be placed on the corresponding substrate at the placement station 164. The control system of the machine is organised so that the appropriate one of the pick-up heads 14 picks up the necessary component from its associated supply of component supply magazines 180 carried by its associated carriage 16 and has the necessary component available at the placement position 186 when required for placement. In order to handle the necessary components it will be necessary to ensure that the tool holder 26 of the appropriate pick-up head 14 is provided with a tool 20 suitbale to handle the required component and it will therefore be necessary to interchange tools carried by the tool support 18 to achieve this. The sequence of movement is arranged to ensure placing of spots of adhesive and picking and placing of components using the correct tools for the various components in the most efficient manner. As will be recalled the tool holder 26 is urged downwardly by air under pressure admitted to the bore 46. The pressure of air in the bore 46 is selected to ensure that an adequate downward pressure is applied to a component placed on a substrate by the pick-up head 14 to ensure good bonding to the substrate, while not exerting sufficient pressure to cause any damage to the component. In order to ensure that the components are positioned in the necessary position and in the correct orientation the control means of the machine is arranged to operate the stepping motor 98 after a component has been picked-up and oriented by the jaws 110, 112, to rotate the component to the necessary orientation at which it is deposited on the substrate. An optical system supplies a confirmation to the machine when rotation of a component through intervals of 90 degrees has been achieved.

Figure 7:
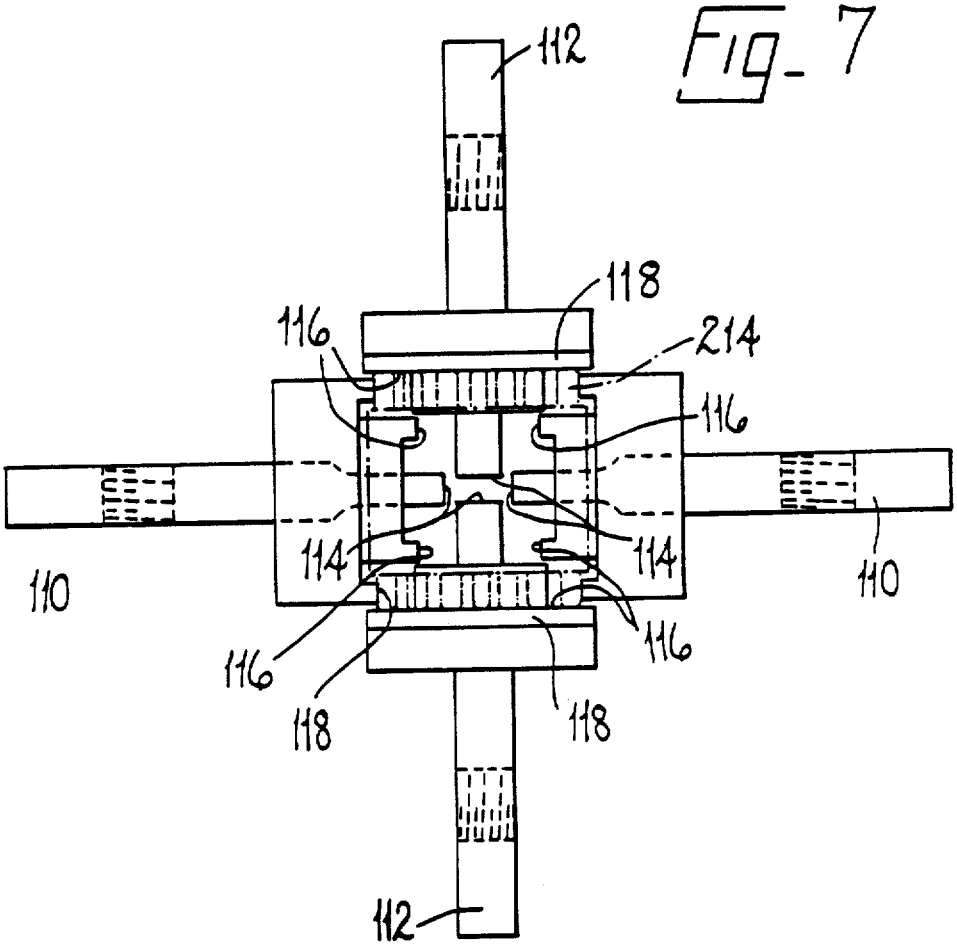
FIG. 7 is a diagrammatic plan view showing the relationship of jaws of the pick-up head when in a closed condition orienting a component.
Figure 8:
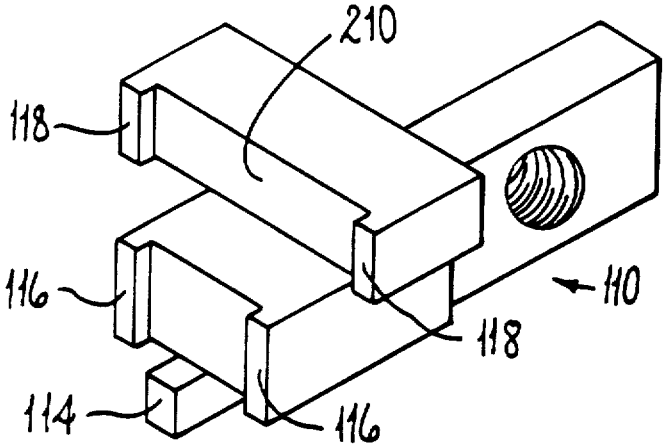
FIGS. 8 and 9 are perspective views of jaws of the pick-up head.
Figure 9:
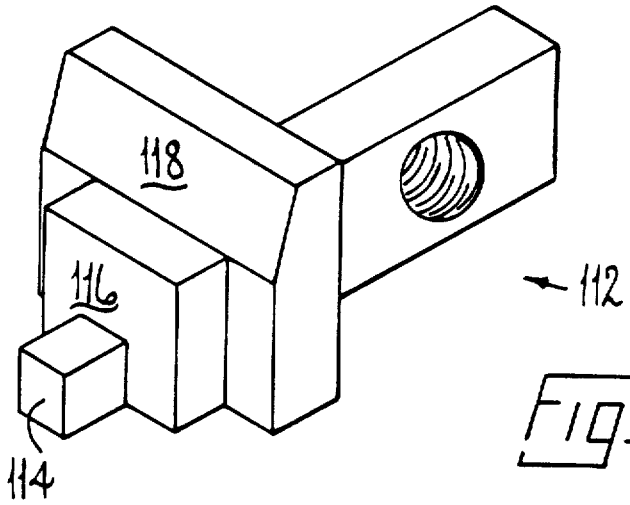

A flow control means, adjustable by the operator before the machine is started to the most appropriate level, is provided to control the inward speed of the jaws 110, 112 (by controlling flow of air to the piston and cylinder arrangements 134, 146). The inward speed of the jaws is preferably set to be as rapid as possible to ensure the most rapid machine cycle time, without risking dislodging components which are held on the tool by vacuum: too rapid an inward movement of the jaw may dislodge components. When a component has been picked from the pick-up position by a tool 20 in the tool holder 26 as aforesaid, the tool holder 26 is raised by a suitable amount under the control of the Servo motor 84 associated therewith until the holder is in the appropriate one of its datum positions, with the component aligned with the appropriate set of jaws 114, 116, 118. As the tool holder 26 approaches the appropriate datum position the piston and cylinder arrangements are operated (according to the programming of the machine) to pivot the arms 120 inwardly, as discussed above, so that as the tool holder 26 reaches the appropriate datum position the component carried by the tool 20 is engaged by the appropriate ones of the pairs of jaws 110, 112. The tool 20 in the holder 26 will have been selected from the tool support 18 to be appropriate for the dimensions of the component to be picked up and the datum position to which the tool holder is moved will ensure that this appropriate tool, the component is positioned correctly in relation to the sets of orienting faces 114, 116, 118. The datum faces 114 are intended to orient the smallest components, the faces 116 to orient intermediate sized components and the faces 118 to orient the largest components which can be handled by the machine. In FIG. 7 the jaws 110, 112 are shown handling a larger component, a so-called S.O. component 213, with leads 214 projecting from the two, opposite, longest sides. In order to make the necessary electrical connections it is essential that these leads are located correctly. The sets 116, 118 of datum faces are shaped to achieve this by providing a recess 210 in the datum faces of the end jaws 110 of the sets 116, 118. As can be seen from FIG. 7, an end portion of the body of the component is received in this recess and the datum faces engage the leads themselves so that orienting is achieved by contacting the leads 214; likewise the set 118 of datum faces of the pair side jaws 112 contact the leads 214. As can be seen from FIGS. 7 and 9 the set 118 of datum faces of the side jaws 112 is slightly angled: the angle is chosen to effect a slight camming action of components contacted by the datum faces 118 of the jaws 112 upwardly towards the tool holder 26 so that the components are pressed firmly against the tool 20 thereby ensuring that when the jaws 110, 112 are opened, the components are maintained in the correct location. As the side jaws 112 are closed against the component slightly before the end jaws 110, this camming action takes place before engagement of the end jaws 110 with the component. The smallest set of orientation faces 114 is used primarily for orienting so-called "chips", small capacitors and resistors. Operation of the jaws is controlled so that the jaws 110 engage the component to be oriented slightly before the jaws 112. Engagement of the component by the appropriate set 114, 116, 118 causes the component to be correctly oriented and positioned on the tool 20. As the jaws orient the component on the end of the tool 20 the head support member 32 is moved in the X direction to carry the head 14 from above the pick-up position to position the head 14 at the placement position 186 whilst at the same time the substrate support 22 is positioning a particular locus of a substrate carried on a pallet 160 in the placement station 164 in register with the placement position 186. When both the substrate 24 and the appropriate head 14 are positioned in the desired positions so that the head 14 is in register with a predetermined position on the substrate 24, the piston and cylinder arrangements are operated to open the jaws 110, 112 thus to release a component, the component being maintained in position on the tool by vacuum applied through the passage 68. The carrier 36 and tool holder 26 are then lowered by the Servo motor 84 and lead screw 72 to a position in which the component is placed on the substrate: the level to which the carrier 36 descends will depend on the thickness of the component to be placed and on the substrate 24 but the carrier 36 normally will descend to the same position relative to the substrate 24, any variation in thickness being accommodated by movement of the holder 26 relative to the carrier 36 against the air pressure in the bore 46. However for very thick components the lead screw operation will be controlled to ensure that the tool holder 26 does not descend too far. The component will be pressed against the predetermined position on the substrate under a preselected pressure determined by the air pressure in the bore 46 and held in that position for a short time until the tool holder 26 is raised. The selected pressure is such as to ensure adequate adhesion of the component in the predetermined position without significant likelihood of damage to the component. If necessary during transport of the pick-head 14 from above the pick-up position to the placement position 186 in its X direction, rotation of the head by the motor 98 will have taken place as hereinbefore mentioned.

After the component has been placed in the desired position on the substrate 24 and the tool is to be raised leaving behind the component it must be ensured that the component remains on the substrate 24 and does not adhere to the tool 20. To ensure separation of the tool 20 from the component a positive air pressure may be introduced into the passage 68, instead of the vacuum, this being necessary where large components are being placed as the tools used in placing larger components tend to not separate readily from the components. In any event, if no positive pressure is used, the vacuum in the passage 68 must be reduced to atmospheric pressure to permit separation: where smaller components are to be placed, use of a positive pressure in the passage 68 may displace the components from the desired position on the substrate and therefore in this instance atmospheric pressure in the passage 68 is preferred.

The noses 202 of the tools 20 are shaped according to the components which they are intended to handle, the larger components being arranged to be handled by tools having noses with a larger datum face 66 than the smaller components. In FIG. 3 the tool shown is particularly appropriate for handling the smaller sized components. The length of the nose 202 projecting beyond the collar 64 to the datum face 66 together with the datum position to which the tool holder 26 is moved by the lead screw 72 will determine which of the sets of datum faces 114, 116, 118 will engage a component carried by the tool when the arms 120 are pivoted to move the jaws 110, 112 inwardly.

From the foregoing it will be seen that the pick-up head of the machine described herein can handle wide range of component sizes without interference by the operator during operation of the machine in a placement operation, the jaws 110, 112 together with the appropriate tools being capable of orienting components of a wide variety of dimensions.

Although the machine has been described hereinbefore in its use in placing components on spots of adhesive applied by the dispenser 208, the components may be placed at the station 164 on adhesive deposits supplied prevously. Likewise adhesive may be applied in the machine for use in subsequent operations.

As previously mentioned the machine may handle cylindrical components: in this case the tool used will have a nose terminating in a recess complementary with the cylindrical component to be handled and any one pair of jaws will be used to locate the component accurately on the tool, the recess being operative to position a component in cooperation with the single pair of jaws. This system will apply to so-called "Melf" components.

I claim:

1. A head for handling electrical components comprising a tool holder, means for moving the holder between a plurality of datum positions and further positions remote therefrom, the holder having means for interchangeably mounting a tool with a datum face thereof positioned at a predetermined position relative to the tool holder, the head further comprising a plurality of orienting jaws mounted for movement towards and away from a component carried by and abutting the datum face of a tool mounted on the tool holder when the holder is in one of the datum positions whereby to engage and orient a component carried by the tool, the jaws having a plurality of spaced sets of cooperating datum faces generally transverse to the plane of the datum face of a tool in the holder, each set of datum faces of the jaws being so disposed as to be capable of orienting a component carried by a tool mounted on the tool holder when the holder is at a corresponding one of said datum positions.

2. A head according to claim 1 in which the means for moving the tool holder is mounted on a housing of the head to move the holder vertically between its datum positions and said positions remote therefrom and the sets of datum faces of the jaws are disposed to cooperate with a tool having its datum face located in a corresponding one of vertically spaced predetermined positions, each corresponding to one of the datum positions of the holder.

3. A head according to claim 2 in which the jaws are carried by arms pivotted on the housing.

4. A head according to claim 1 in which each set of datum faces of the jaws is constructed and arranged for operation on components within a range of dimensions.

5. A head according to any one of the preceding claims in which the tool holder has a socket in which a shank portion of a tool can be received to mount a tool on the holder.

6. A head according to claim 5 in which the tool holder comprises retaining means which is resiliently biased into a recess in the shank of a tool received in the socket whereby to retain the tool on the holder.

7. A head according to claim 6 in which the retaining means comprises a plurality of balls held captive in the holder but projecting into the socket, the balls engaging in a recess in the shank to retain the tool on the holder.

8. A head according to claim 5 comprising a locating face against which a locating face of a tool abuts when a tool is mounted on the holder whereby to locate the datum face of the tool relative to the holder so that the datum face of the tool is at said predetermined position.

9. A head according to claim 1 in which the means for moving the tool holder comprises a lead screw driven by a motor.

10. A machine for handling electrical components comprising a head according to claim 1, a tool support for supporting a plurality of tools and means for relatively moving the head and tool support whereby to mount a preselected tool carried by the tool support on the tool holder.

11. A machine according to claim 10 so constructed and arranged as to deposit a first tool from the tool holder in a preselected position of the tool support and then to mount a second tool from a second preselected position of the tool support on the tool holder.

12. A machine comprising a head according to claim 5 comprising a tool support for supporting a plurality of tools and means for relatively moving the head and tool support whereby to mount a preselected tool carried by the tool support on the tool holder in which the tool support comprises a housing by which tools are supported in a plurality of positions with their shanks projecting and the means for relatively moving the head and tool support is effective in the operation of the machine to engage the shank of a tool in a preselected one of the positions in the socket of the tool holder whereby to mount a preselected tool in the holder.

13. A machine according to claim 12 in which the tool support comprises means for engaging a tool carried by the tool holder, separating it from the holder and depositing it in a preselected position of the tool support.

14. A machine according to any one of claims 10 to 13 comprising means for moving the tool support along a first path and means for moving the head along a second path at right angles to the first path to align the tool holder with a preselected one of the tools carried by the tool support and means for moving the tool holder when so-aligned into engagement with the preselected tool whereby to mount the tool in the holder.

15. A machine according to any one of claims 10 to [14] *13* comprising means for supplying components to the head, a support for a substrate on which components are to be placed, and means for effecting relative movement between the support and the head whereby to ensure that the head is in register with a predetermined position at which a component is to be placed.

16. A machine for handling electrical components comprising a head according to claim 1, a support for a substrate on which components are to be placed a carriage mounting a plurality of component magazines and a tool support, means for moving the substrate support along a first path and a second path at rightangles to the first, means for moving the carriage along a path parallel with said first path whereby to present a component at an outlet position of a preselected one of the magazines at a pick-up position or to present the tool support in its tool-loading position, and means for moving the head along a path at rightangles to the first path between a placement position at which the head is aligned by movement of its substrate support with a predetermined position of a of the substrate, a preselected position on the tool support which has been moved into its tool-loading position by the carriage, or with the pick-up position, whereby to place a component on the substrate at said predetermined position, to deposite a tool on, or mount a tool from, said preselected position on said tool support, or to pick-up a component at the pick-up position respectively.

17. A machine according to any one of claims 10 to 13 *or 16* comprising means for connecting a passage opening through the datum face of a tool mounted in the tool holder to vacuum.

18. A machine according to any one of claims 10 to [17] *13 or 16* comprising means for rotating the tool holder of a head through a predetermined angle.

19. A head for handling electrical components comprising two pairs of opposed jaws, each jaw having a plurality of orienting faces, the orienting faces of each jaw being disposed to cooperate with corresponding orienting faces of the other jaws of the head providing a plurality of sets of orienting faces as the pairs of jaws are moved towards one another in the operation of the head, *means for moving each pair of jaws in directions perpendicular to each other to engage* a component between the jaws [being engaged] by the orienting faces of *at least* one of the sets as the jaws of each pair are moved towards one another whereby to orient the components in a preselected orientation.

20. A head according to claim 19 in which the jaws of one pair are constructed to interengage between the jaws of the other pair as the jaws of each pair are moved towards one another.

21. A head according to either one of claims 19 and 20 wherein a recess to receive a body portion of a component is provided in the datum faces of at least one set of datum faces of one pair of jaws so that the datum faces engage leads of the component.

22. A head according to any one of claims 19 [to 21] *and 20* wherein the datum faces of at least one set of faces, on at least one pair of jaws are inclined whereby to provide a camming action as the jaws are closed on a component urging the component into engagement with a tool holder of the head.

23. A [set of jaws for a] head according to claim

[18] *19 wherein* each jaw [having] *within a pair of jaws has* a plurality of orienting faces, each orienting face being arranged to cooperate with corresponding orienting faces of other jaws whereby to provide a plurality of sets of orienting faces.

* * * * *